US00PP27050P2

(12) United States Plant Patent
Garner

(10) Patent No.: US PP27,050 P2
(45) Date of Patent: Aug. 9, 2016

(54) ***ALOCASIA* PLANT NAMED 'REGAL SHIELDS'**

(50) Latin Name: ***Alocasia odora*×*Alocasia reginula***
Varietal Denomination: Regal Shields

(71) Applicant: LariAnn Garner, Florida City, FL (US)

(72) Inventor: LariAnn Garner, Florida City, FL (US)

( * ) Notice: Subject to any disclaimer, the term of this patent is extended or adjusted under 35 U.S.C. 154(b) by 93 days.

(21) Appl. No.: 14/121,028

(22) Filed: Jul. 22, 2014

(51) Int. Cl.
*A01H 5/12* (2006.01)

(52) U.S. Cl.
USPC ..... Plt./373

(58) Field of Classification Search
USPC ..... Plt./373
See application file for complete search history.

(56) References Cited

PUBLICATIONS

Aroidia Research 2013 New Releases from Aroidia, retrieved on Dec. 16, 2015, retrieved from the Internet at <http://aroidiaresearch.org/releases2.htm> 1 p.*

* cited by examiner

*Primary Examiner* — June Hwu
(74) *Attorney, Agent, or Firm* — Penny J. Aguirre

(57) ABSTRACT

A new cultivar of *Alocasia* plant, 'Regal Shields', that is characterized by its small, compact plant habit, its cold resistance to the winter conditions in southern Florida, its adaptability to shade or sun conditions, its thick and durable leaves, its exhibits mature leaves that are dark green in color suffused with purple with green veins on the upper surface and purple in color with yellow-green veins on the lower surface with the color persistent and consistent, and its ease of growth during production.

3 Drawing Sheets

Botanical classification: *Alocasia odora*×*Alocasia reginula.*

Cultivar designation: 'Regal Shields'.

BACKGROUND OF THE INVENTION

The present invention, *Alocasia* 'Regal Shields', relates to a new and distinct interspecific hybrid of *Alocasia*, hereinafter referred to by its cultivar name, 'Regal Shields'. 'Regal Shields' is a new tropical plant used as a landscape and container plant.

The new cultivar was derived from a controlled breeding program conducted by the Inventor at a nursery in Florida City, Fla. The overall purpose of the breeding program is to make selections of *Alocasia* plants with unique foliage that are cold resistant and durable with a good growth rate in Florida. 'Regal Shields' arose from a cross make in 2007 between an unnamed plant of *Alocasia odora* as the female parent and an unnamed plant of *Alocasia reginula* as the male parent. 'Regal Shields' was selected as a single unique plant in 2013 from amongst the seedlings derived from the above cross.

Asexual propagation of the new cultivar was first accomplished using corm division by the Inventor in Florida City, Fla. in 2008. Asexual propagation by corm division and tissue culture using meristem tissue of the new cultivar has shown that the unique features of the new cultivar are stable and reproduced true to type in successive generations.

SUMMARY OF THE INVENTION

The following traits have been repeatedly observed and represent the characteristics of the new cultivar. These attributes in combination distinguish 'Regal Shields' as a new and unique cultivar of *Alocasia.*

1. 'Regal Shields' exhibits a small, compact plant habit.
2. 'Regal Shields' exhibits cold resistance to the winter conditions in southern Florida.
3. 'Regal Shields' exhibits adaptability to shade or sun conditions.
4. 'Regal Shields' exhibits, thick, durable leaves.
5. 'Regal Shields' exhibits mature leaves that are dark green in color suffused with purple with green veins on the upper surface and purple in color with yellow-green veins on the lower surface with the color persistent and consistent.
6. 'Regal Shields' has been shown to be easy to grow in production.

The female parent of 'Regal Shields', an unnamed plant of *Alocasia odora*, differs from 'Regal Shields' in being completely green in color, in being larger in overall size, and in having leaves that are thinner. The male parent of 'Regal Shields', an unnamed plant of *Alocasia reginula*, differs from 'Regal Shields' in being smaller in overall size, in having leaves that are thicker, in being more difficult to grow, in being susceptible to cold, and in having more intense leaf coloration. 'Regal Shields' can be most closely compared to typical plants of *Alocasia wentii* and the *Alocasia gageana* cultivar 'California' (not patented). Typical plants of *Alocasia wentii* are similar to 'Regal Shields' in having a small, compact growth habit and in having leaves that are purple in color on the lower surface. Typical plants of *Alocasia wentii* differs from 'Regal Shields' in having leaves that are thinner, in having leaves that are more elongated in shape, and in having less conspicuous vein coloration on the lower surface of the leaves. 'California' is similar to 'Regal Shields' in having a small, compact growth habit and in having cold resistance to winter conditions in southern Florida. 'California' differs from 'Regal Shields' in being completely green in color, in producing very large quantities of offsets, and in having leaves that are thinner and lighter in color.

BRIEF DESCRIPTION OF THE DRAWINGS

The accompanying colored photographs illustrate the overall appearance and distinct characteristics of the new *Alocasia*, 'Regal Shields'.

The photograph in FIG. 1 was taken of a 4 month old plant of 'Regal Shields' as grown outdoors in a one-gallon container in Florida City, Fla.

Figure 1:
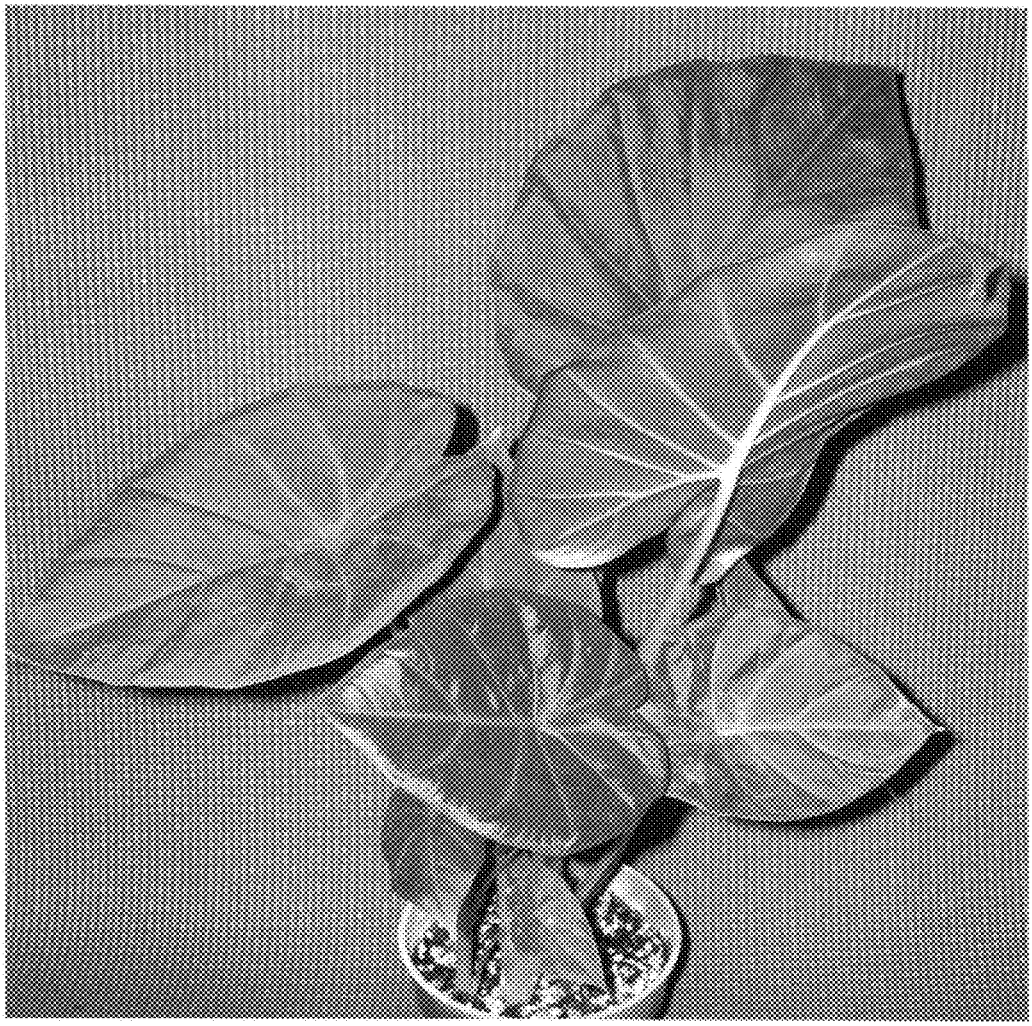
FIG. 1 provides an overall view of the foliage and plant habit of a young plant of 'Regal Shields'.
Figure 2:
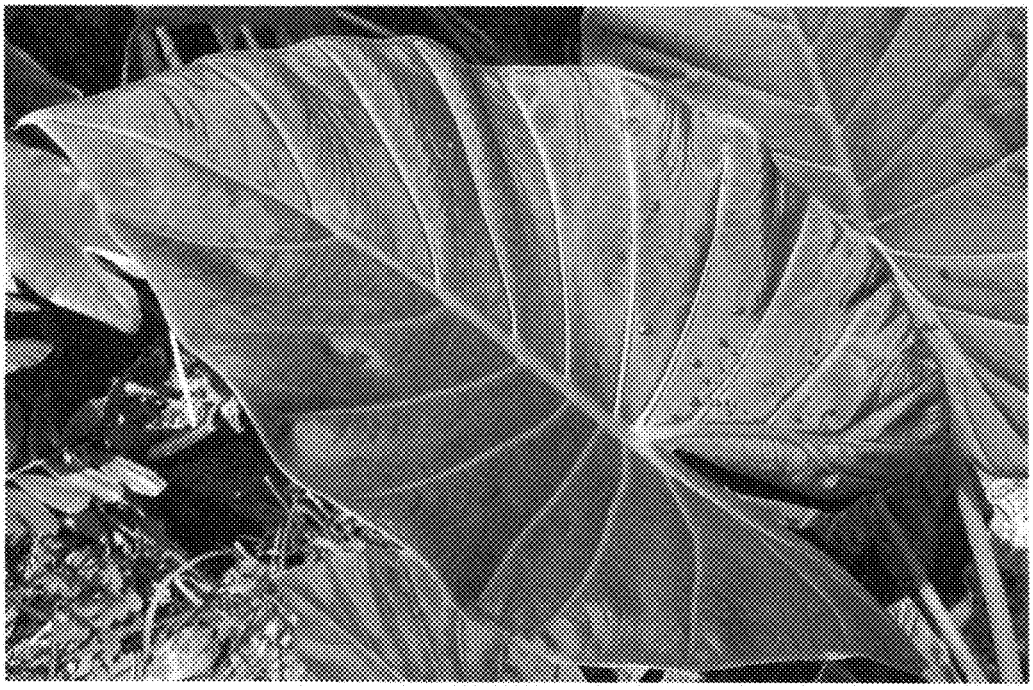
Figure 3:
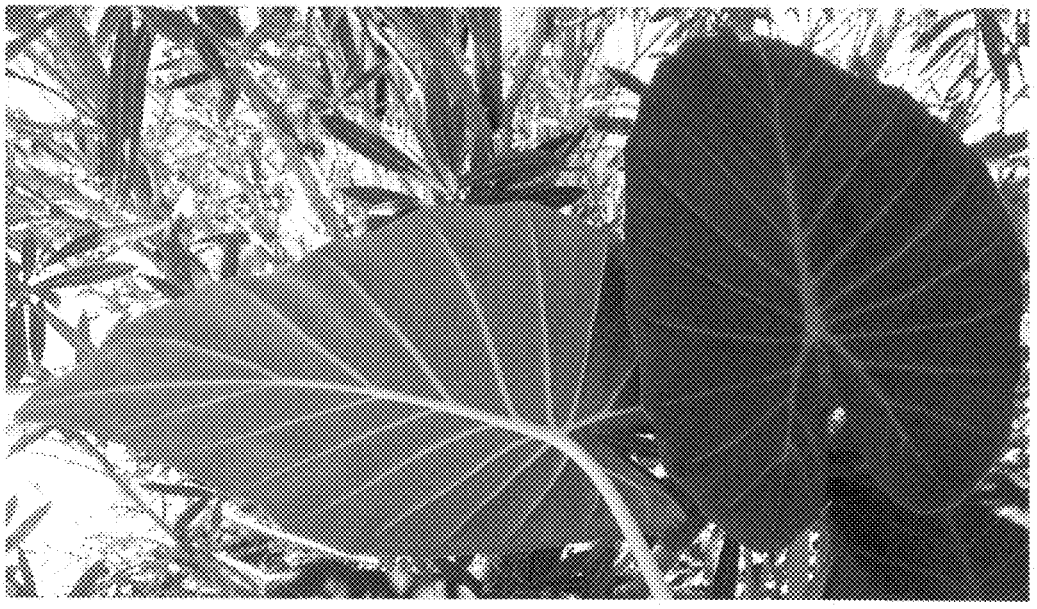

The photographs in FIG. 2 and FIG. 3 were taken of a 6 month-old plant of 'Regal Shields' as grown outdoors in a two-gallon container in Florida City, Fla.

The photograph in FIG. 2 provides a close-up view of the upper surface of a young leaf of 'Regal Shields'.

The photograph in FIG. 3 provides a close-up view of the upper and lower surfaces of mature leaves of 'Regal Shields'.

Figure 4:
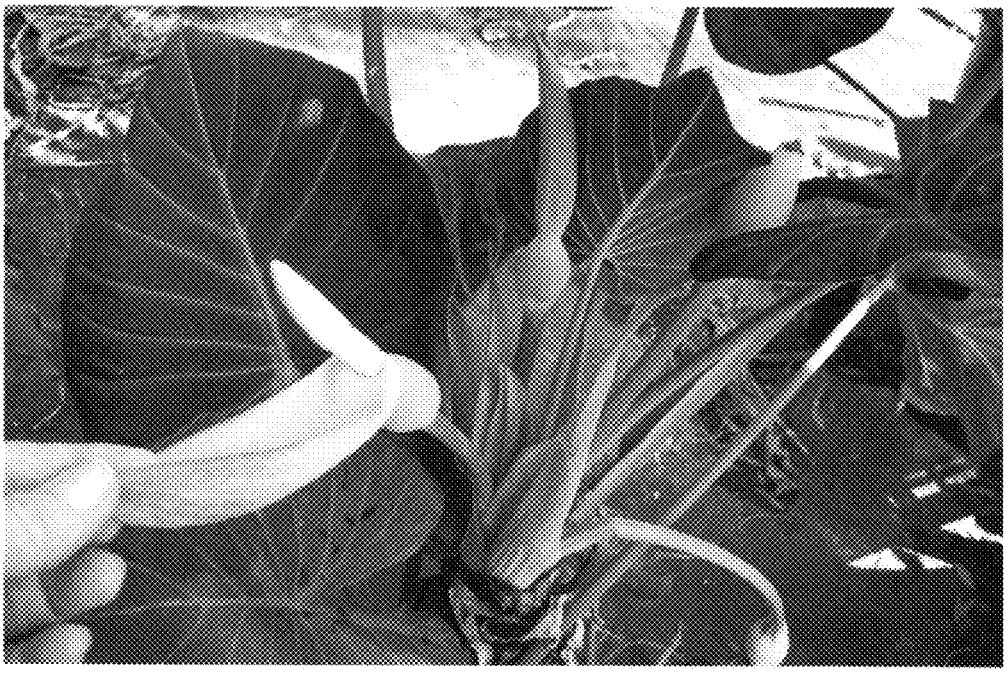

The photograph is FIG. 4 provides a close up view of an inflorescence of 'Regal Shields'.

The colors in the photographs are as close as possible with the photographic and printing technology utilized and the color values cited in the Detailed Botanical Description accurately describe the colors of the new *Alocasia*.

DETAILED BOTANICAL DESCRIPTION OF THE PLANT

The following is a detailed description of 6 month-old plants of the new cultivar as grown outdoors in full sun under 2 mm poly greenhouse plastic in a two-gallon containers in Florida City, Fla. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Tropical perennial herb.

*Plant habit.*—Upright.

*Height and spread.*—30 cm to 1.2 m in height and 61 cm to 91 cm in width.

*Cold hardiness.*—At least to U.S.D.A. Zone 10.

*Diseases and pests.*—Moderately resistant to spider mites.

*Roots.*—Fleshy.

*Propagation type.*—Tissue culture using meristem tissue (preferred), corms, offsets.

*Corm.*—Circular in shape, surface texture is slightly glossy at apex and bark-like and nubby at base, an average of 3 cm in diameter and 6 cm in height, a blend of 166A and 166B with an underlay of N137A in color, cormel; surface texture is dull and bark-like, oblong in shape, an average of 4 mm in width and 3 mm in height, 166A in color.

*Growth rate.*—Moderately vigorous.

*Stem description.*—Rhizome-like trunk formed at the base of the petioles with age.

Foliage description:

*Leaf shape.*—Cordate-sagittate.

*Leaf division.*—Single.

*Leaf base.*—Sagittate, deeply cut; lobes about 5 cm in length and width.

*Leaf apex.*—Cuspidate and with tip downward.

*Leaf venation.*—Pinnate, color: young leaves upper surface; 144C, mature upper surface; 141C, young and mature leaves lower surface; 144D, conspicuous on both surfaces.

*Leaf margins.*—Slightly undulate.

*Leaf attachment.*—Petiolate.

*Leaf arrangement.*—Alternate.

*Leaf surface.*—Upper surface; coriaceous, glabrous and dull, lower surface; coriaceous, glabrous and satiny.

*Leaf orientation.*—Held horizontal to slightly upward.

*Leaf color.*—Young leaves upper surface; 143A lightly suffused with 187A, young leaves lower surface a blend of N186C and N187A, mature leaves upper surface; 139A suffused with 187A, mature leaves lower surface; N187A to N187C lightly suffused with 151B.

*Leaf size.*—Up to 23 cm in length and about 15.2 cm in width.

*Petioles.*—Held erect to semi-erect, about 23 cm in length, 6 mm in distal diameter, and 1 cm in basal diameter, glabrous surface, 144A to 144C with tiny spots of N187A in color, rhizome-like base; about 5 cm in length and 2.7 cm in width, comprised of petiole scales, surface is rough and paper-like, color is a blend of N167B and 163A to 163C.

Inflorescence description:

*Inflorescence type.*—Spadix surrounded by a spathe, male portion held above female portion, only female flowers were developed.

*Inflorescence size.*—Average of 9 cm in length and 2 cm in diameter.

*Inflorescence bud.*—Upper portion lanceolate in shape with lower portion elliptic, an average of 10 cm in length and 2 cm in width, upper portion 143B in color and slightly suffused with N77C, lower portion 145B in color, glabrous surface.

*Flower fragrance.*—Acidic fragrance.

*Lastingness of inflorescence.*—Inflorescence blooms intermittently during the bloom period, bloom period though out summer when grown outdoors, individual flowers last about 2 to 3 weeks.

*Inflorescence/flower quantity.*—Intermittent throughout the bloom season, sets of 3 or more at one time, an average of 70 female flowers per spadix, male flowers were undeveloped.

*Spathe.*—Hooded, bract, subtending spadix, 12 cm in length and 3 cm in width, free portion: wedge-shaped, entire margin, apiculate apex, glabrous and dull on both surfaces, 7 cm in length and 3 cm in width, lasts 5 to 7 days, color: when opening and fully open on inner and outer rear surface; 143B and slightly suffused with N77C, fading to 10D before shriveling, lower portion; surrounds ovary, elliptic in shape, 4 cm in length and 2 cm in width, 145B in color, glabrous and dull on both surfaces.

*Spadix.*—Comprised of appendix, male zone, sterile zone, and female zone, in total 10 cm in length and up to 1.5 cm in width, appendix; lanceolate in shape, 4 cm in length and 1 cm in width, narrowly acute apex, brain-like texture, 145C in color, male portion; cylindrical in shape, 2 cm in length and 8 mm in width, 158C in color, comprised on flattened circular stamens, glabrous surface, sterile portion; cylindrical in shape with center indented, glabrous surface, 158C in color, 1 cm in length and 5 mm in width, female portion; conical in shape, about 1.1 cm in diameter and 2 cm in length, surface comprised of raised irregular shaped stigmas, 145C in color.

*Peduncle.*—Grows from base of plant, up to 16 cm in length and 1.1 cm in diameter, held at 20° angle, durable and strong, a blend of 145A and N77C in color, glabrous surface.

Reproductive organs:

*Gynoecium.*—Stigmas are 145C in color and about 1.5 mm in diameter, ovaries is rounded in shape, about 2 mm in diameter, glossy surface and 145B in color.

*Androecium.*—Stamens flattened circular in shape, about 1.5 mm in diameter, 158C in color.

*Fruit and seed.*—None observed to date.

It is claimed:

1. A new and distinct cultivar of *Alocasia* plant named 'Regal Shields' as herein illustrated and described.

* * * * *